United States Patent [19]

Bates et al.

[11] 4,091,811

[45] May 30, 1978

[54] NEEDLE COVER

[75] Inventors: David A. Bates, Libertyville; Angelo T. Capritta, Schaumburg, both of Ill.

[73] Assignee: Baxter Travenol Laboratories, Inc., Deerfield, Ill.

[21] Appl. No.: 741,875

[22] Filed: Nov. 15, 1976

[51] Int. Cl.² ............................................. A61M 5/14
[52] U.S. Cl. .................................. 128/214.4; 128/221
[58] Field of Search ............... 128/218 R, 218 N, 220, 128/221, 215, 214.2, 214 R, 216, 213, 214.4

[56] References Cited

U.S. PATENT DOCUMENTS

| | | | |
|---|---|---|---|
| 3,523,530 | 8/1970 | Pagones | 128/214 |
| 3,734,095 | 5/1973 | Santomieri | 128/221 X |
| 3,980,083 | 9/1976 | Elliott | 128/220 |

Primary Examiner—John D. Yasko
Attorney, Agent, or Firm—Henry W. Collins; Paul C. Flattery; Garrettson Ellis

[57] ABSTRACT

A needle cover for a blood collection needle or the like comprises a first sleeve positioned about a pointed hypodermic needle. The first sleeve is removably carried by a hub, which also carries the needle. In accordance with this invention an inner sleeve is provided, positioned within the first sleeve and about the point of the needle. The inner sleeve is free of mechanical attachment to the first sleeve so that, upon rotation of the outer sleeve for its removal from the hub, the inner sleeve does not rotate with the first sleeve. Accordingly, the danger of the pointed needle scouring out and retaining bits of plastic from the sleeve is eliminated.

4 Claims, 3 Drawing Figures

NEEDLE COVER

BACKGROUND OF THE INVENTION

Conventional blood bags carry a blood collection needle which is attached to a hub, to preserve sterility of the needle. A removable sheath or needle cover is positioned about the needle, and removably attached to the hub.

Generally, the sheath is made out of rubber or plastic, and may be removed by twisting. In one prior art embodiment (Pagones U.S. Pat. No. 3,523,530) the sheath is formed integrally with the hub, being connected thereto by a thin, frangible ring of plastic through which the needle protrudes from the hub into the sheath. Accordingly, for removal of the sheath, it is merely twisted to break the frangible plastic ring.

One serious drawback to this sort of arrangement is that, upon twisting of the sheath, it is possible for the pointed needle end to dig into the inner wall of the sheath, scouring out a small piece of plastic which may remain within the hollow-pointed end of the needle, or on a sharp edge. This is obviously most undesirable, since the plastic piece may be implanted into the arm of a blood donor if it is not noticed. Even if it is noticed, it will have to be removed by the user, which tends to threaten the sterility of the needle.

As a further disadvantage relating to the needles of blood bags and the like, in many designs, the blood preservative such as ACD or CPD can pass upwardly through the tip of the needle to wet the outside thereof. This can result in an unpleasant burning sensation in the skin during veinopuncture.

In accordance with this invention, the above disadvantages are eliminated to provide a more reliable puncturing needle, free of plastic shards or of danger of blunting the needle through scraping contact with the needle cover during removal, where the needle is sealed so that its exterior is not wetted by the contents of the blood bag.

It is also contemplated that the invention of this application can be used for other needle covers, such as for administration sets and the like which are used for purposes other than blood collection.

DESCRIPTION OF THE INVENTION

In this invention, a needle cover is provided which comprises a first sleeve positioned about a pointed hypodermic needle. The first sleeve is removably carried by a hub, which also carries the needle.

In accordance with this invention, an inner sleeve is positioned within the first sleeve and about the point of the needle. The inner sleeve is free of mechanical attachment to the first sleeve, whereby, upon rotation of the outer sleeve for its removal, the inner sleeve does not rotate with the first sleeve. Accordingly, scouring of the inside of the inner sleeve by the needle point is prevented despite the rotation and bending of the needle cover for removal. At the same time, the inner sleeve can serve as a seal around the pointed end of the needle, so that the contents cannot spill out of the lumen of the needle at the pointed end to wet the exterior of the needle. Accordingly, the stinging sensation associated upon veinopuncture with that phenomenon can be reduced.

Typically, the inner end of the first sleeve defines a constriction which is sufficient in size to prevent passage of the inner sleeve through the inner end thereof.

Also, the first sleeve may carry a plug occluding its outer end, and the inner sleeve defines a closed outer end. To reduce friction, the inner end of the plug and the outer end of the inner sleeve may each define a separate shape, permitting single-point contact therebetween. For example, one of the two ends mentioned above may be of concave, conical shape of an angle which is greater than the other end, which then may be of convex, conical shape of a lesser angle, as illustrated in the drawings.

Referring to the drawings.

Figure 1:
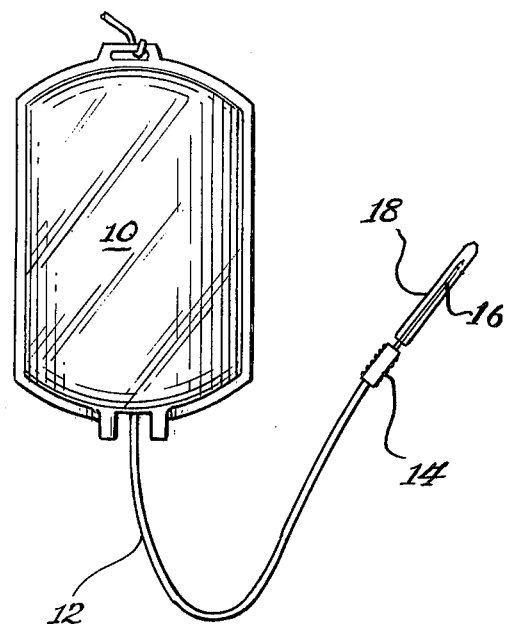
FIG. 1 is an elevational view of a blood bag carrying a veinopuncture needle for blood collection at the end of flexible, blood compatible tubing, utilizing the needle cover of this invention.

Referring to the drawings, blood bag 10, which may be of conventional construction, carries blood collection tubing 12, communicating with the interior thereof and terminating in a needle hub 14, which may be of molded plastic. Needle 16 is carried by needle hub, passing therethrough. Generally, the hub 14 is injection molded or the like about needle 16.

Figure 2:
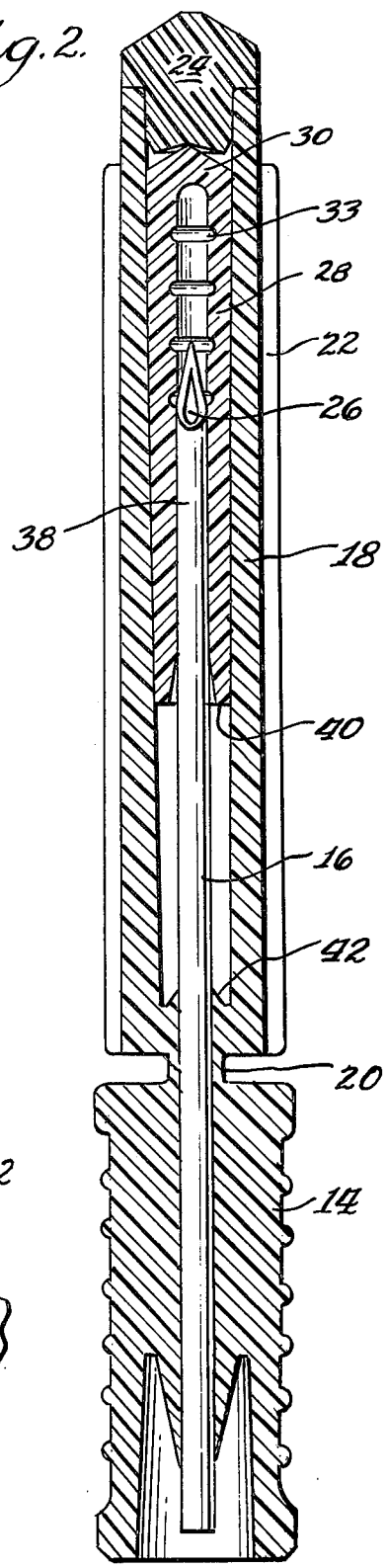
FIG. 2 is a greatly enlarged longitudinal sectional view of the veinopuncture needle and hub, utilizing this invention.

First sleeve 18 is shown in FIG. 2 in the specific embodiment to be integral with hub 14 and made in the same molding process. It is connected to hub 14 by a thin, annular frangible ring or collar 20, and carries several veins 22 to facilitate gripping of the hub for twisting and bending removal thereof by the rupturing of thin plastic collar 20. First sleeve 18 carries a plug 24, which may be conventionally sealed to the end of the first sleeve. Alternatively, first sleeve 18 may be closed in any other manner desired.

Positioned within first sleeve 18, in a position to enclose point 26 of needle 16, is an inner sleeve 28 defining a closed end 30.

Annular transverse grooves 33 are provided to primarily facilitate molding of inner sleeve 28 by providing means for better retention on the core pin.

Figure 3:
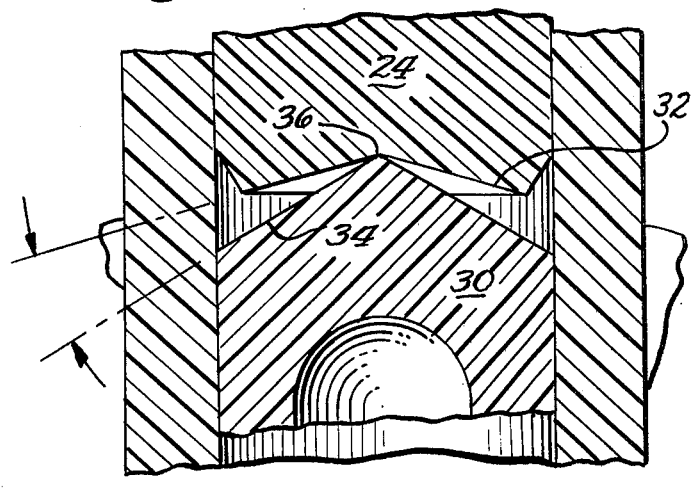
FIG. 3 is a greatly enlarged longitudinal sectional view of a portion of FIG. 2.

The inner end 32 of plug 24 is of concave conical shape, a transverse section of which defines an obtuse angle as shown in FIG. 3. The outer, closed end 30 of inner sleeve 28 defines a convex conical surface 34 in which a cross section thereof defines an angle which is less than the obtuse angle of a cross section of surface 32, so that a point contact 36 between the two surfaces is provided.

Inner sleeve 28 is proportioned so that its inner diameter grippingly seals needle 16, and its outer diameter provides a relatively loose sliding fit within the inner diameter of the first sleeve 18, to encourage sliding motion between first sleeve 18 and inner sleeve 28 rather than between inner sleeve 28 and needle 16, when first sleeve 18 is rotated.

Accordingly, as first sleeve 18 is manually rotated to rupture neck 20 for removal of the sleeve, inner sleeve 28 does not rotate with it. Neck 20 can be ruptured for removal of the sleeve without any relative rotational motion between point 26 of the needle and the inner sleeve 28, the rotation taking place between the inner sleeve and first sleeve 18. Thus, the problem of plastic scraping taking place at point 26 is eliminated.

At the same time, inner sleeve 28 provides sealing along area 38 of needle 16, to prevent any liquid passing from inside of the needle through its end to the exterior of the needle. Thus, the needle, immediately after removal of the cover, may be dry on the outside, for the avoidance of the undesirable stinging sensation upon veinopuncture.

After rupturing of collar portion 20, first sleeve 18 can be removed. Because inner sleeve 28 is proportioned so that it grips needle 16 more tightly than first sleeve 18 grips inner sleeve 28, inner sleeve 28 initially may not slide outwardly as first sleeve 18 is manually removed from the needle. However, when the inner end 40 of the inner sleeve 28 comes into contact with constriction 42 in the bore of first sleeve 18, as sleeve 18 is withdrawn from the needle, inner sleeve 28 is also forced to be withdrawn from the needle to expose it for use.

By way of example, for a 16 gauge needle, the radius of the inner diameter of first sleeve 18 adjacent its outer end may be 0.160 inch. The bore of sleeve 18 may taper inwardly at an angle of about 1°, moving toward the inner end thereof, to facilitate molding. The inner diameter of inner sleeve 28 may be 0.066 inch, while its outer diameter may be 0.12 inch. If desired, the inner sleeve 28 may be proportioned to stretch slightly when threaded upon needle 16, while preferably retaining at least 0.01 inch less outer diameter than the inner diameter of first sleeve 18, to permit the loose, sliding relationship between sleeve 18 and 28.

The plastic parts utilized in this invention may be made of polyvinylchloride plastisol of a fairly stiff grade, if desired.

The above has been offered for illustrative purposes only, and is not to limit the invention of this application, which is as defined in the claims below.

That which is claimed is:

1. In a needle cover which comprises a first sleeve positioned about a pointed hypodermic needle, said first sleeve being removably carried by a hub which also carries said needle, the improvement comprising, in combination:

an inner sleeve positioned within said first sleeve and about the point of said needle, said inner sleeve being free of mechanical attachment to said first sleeve, and means connecting said first sleeve to said hub, whereby, upon rotation of said first sleeve for removal thereof, said inner sleeve does not rotate with said first sleeve.

2. The needle cover of claim 1 in which the inner end of said first sleeve defines a constriction sufficient to prevent passage of said inner sleeve.

3. The needle cover of claim 2 in which said first sleeve carries a plug occluding its outer end, and said inner sleeve defines a closed outer end, the inner end of said plug and the outer end of said inner sleeve each defining a separate shape permitting singlepoint contact therebetween.

4. The needle cover of claim 3 in which said first sleeve is integrally attached to said hub by a thin, frangible neck portion, breakable on rotation of said first sleeve.

* * * * *